United States Patent [19]

Resnick

[11] 4,081,466

[45] Mar. 28, 1978

[54] CATALYTIC REACTION OF HEXAFLUOROPROPYLENE EPOXIDE WITH A KETONE OR ACID FLUORIDE

[75] Inventor: Paul Raphael Resnick, Wilmington, Del.

[73] Assignee: E. I. Du Pont de Nemours and Company, Wilmington, Del.

[21] Appl. No.: 697,629

[22] Filed: Jun. 18, 1976

Related U.S. Application Data

[63] Continuation-in-part of Ser. No. 564,483, Apr. 2, 1975, abandoned.

[51] Int. Cl.² .............................................. C07C 51/58
[52] U.S. Cl. ................................................. 260/544 F
[58] Field of Search ..................................... 260/544 F

[56] References Cited

U.S. PATENT DOCUMENTS

| 3,250,808 | 5/1966 | Moore et al. | 260/543 F |
| 3,940,402 | 2/1976 | Middleton | 260/293.63 |

*Primary Examiner*—Norman Morgenstern

[57] ABSTRACT

In the catalytic reaction of hexafluoropropylene epoxide with a ketone or acid fluoride to yield an acid fluoride containing fluorocarbon ether, a catalyst of a sulfonium salt is employed.

6 Claims, No Drawings

CATALYTIC REACTION OF HEXAFLUOROPROPYLENE EPOXIDE WITH A KETONE OR ACID FLUORIDE

RELATED APPLICATION

The present application is a continuation-in-part of copending application Ser. No. 564,483 filed Apr. 2, 1975 now abandoned.

BACKGROUND OF THE INVENTION

The present invention is directed to the catalytic formation of fluorocarbon ethers which are in addition acid fluorides.

Moore et al., U.S. Pat. No. 3,250,808 issued May 10, 1966, discloses the catalytic preparation of fluorocarbon ethers by the reaction of hexafluoropropylene epoxide with fluoroalkanoic acid fluorides and fluoroalkanones. Compounds falling within the disclosure of this patent would include those represented by the formula

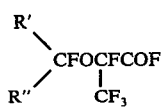

wherein R' and R" represent various fluorine containing groups.

A suitable catalyst in the reaction procedure of the Moore et al. patent is activated charcoal or a high energy, particulate ionizing radiation. A further catalyst disclosure in the patent is the use of monovalent metal fluorides, particularly alkali metal fluorides, quaternary ammonium fluorides and alkali metal perfluoroalkoxides.

SUMMARY OF THE INVENTION

The present invention is directed to the catalyzed reaction of hexafluoropropylene epoxide with a ketone or an acid fluoride involving the use of a catalyst of a sulfonium salt.

The derived reaction product from hexafluoropropylene epoxide and the ketone or acid fluoride is an acid fluoride containing ether of the formula:

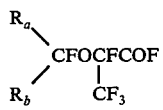

wherein $R_a$ and $R_b$ each independently of the other is fluorine, a fluoroalkyl group or a sulfonyl substituted fluoroalkyl group of one to 14 carbon atoms, a fluoroalkoxy or a sulfonyl substituted fluoroalkoxy group of one to 14 carbon atoms, a fluoroalkoxyalkyl group or a sulfonyl substituted fluoroalkoxyalkyl group of one to 14 carbon atoms and one to six oxygen atoms. The formula for the ketone and acid fluoride is

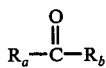

with $R_a$ and $R_b$ as previously defined.

A catalyst of a sulfonium salt has been found to give excellent results in the formation of the desired compounds. An example of a suitable class of sulfonium salts is $R_1R_2R_3S^+X^-$, wherein $R_1$, $R_2$ and $R_3$ each independently of the other is an alkyl group of one to 12 carbon atoms and X, is F, $(CH_3)_3SiF_2$, Cl, Br, I, CN, NCO, NCS, $NO_2$ and $N_3$. A preferred class of sulfonium salts is of the formula $$(R^1R^2N)(R^3R^4N)(R^5R^6N)S^+X^-$$

wherein the R groups individually are alkyl of up to 20 carbon atoms each alkyl having at least 2 alpha-hydrogen atoms, with the proviso that any or all of the pairs $R^1$ and $R^2$, $R^3$ and $R^4$ and $R^5$ and $R^6$ taken together with the nitrogen atom to which they are attached form a pyrrolidino or piperidino ring, any substituents being alkyl of up to 8 carbon atoms, and X is selected from the group consisting of $(CH_3)_3SiF_2$, Cl, Br, I, CN, NCO, NCS, $NO_2$ and $N_3$.

DETAILED DESCRIPTION OF THE INVENTION

The present process in the reaction of hexafluoropropylene epoxide with a ketone or an acid fluoride follows the teachings of U.S. Pat. No. 3,250,808 with the critical distinction of a different catalyst. The catalyst employed herein is a sulfonium salt. Although the starting catalytic material in the reaction procedure is a sulfonium salt, e.g., a sulfonium halide, conversion to sulfonium fluoride is considered likely to occur during the reaction regardless of the salt of the form of the beginning catalyst. Therefore, it is understood in the present disclosure that the form of the catalyst may be different as the reaction progresses.

The ketone or acid fluoride reactant is of the formula

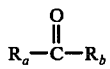

wherein $R_a$ and $R_b$ each independently of the other is fluorine, a fluoroalkyl group or a sulfonyl substituted fluoroalkyl group of one to 14 carbon atoms, a fluoroalkoxy or a sulfonyl substituted fluoroalkoxy group of one to 14 carbon atoms, a fluoroalkoxyalkyl group or a sulfonyl substituted fluoroalkoxyalkyl group of one to 14 carbon atoms and one to six oxygen atoms.

The catalyzed reaction of hexafluoropropylene epoxide with the ketone or acid fluoride results in the formation of the compound of the formula

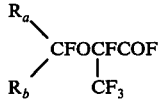

with $R_a$ and $R_b$ as previously defined.

A preferred group of sulfonium salt catalysts is of the formula $R_1R_2R_3S^+X^-$, wherein $R_1$, $R_2$ and $R_3$ each independently of the other is an alkyl group of one to 12 carbon atoms and more preferably one to five carbon atoms and X, is F, $(CH_3)_3SiF_2$, Cl, Br, I, CN, NCO, NCS, $NO_2$ and $N_3$. A preferred class of sulfonium salts is of the formula $$(R^1R^2N)(R^3R^4N)(R^5R^6N)S^+X^-$$

wherein the R groups individually are alkyl of up to 20 carbon atoms each alkyl having at least 2 alpha-hydrogen atoms, with the proviso that any or all of the parts $R^1$ and $R^2$, $R^3$ and $R^4$ and $R^5$ and $R^6$ taken together with the nitrogen atom to which they are attached form a pyrrolidino or piperidino ring, any substituents being alkyl of up to 8 carbon atoms, and X is selected from the group consisting of $(CH_3)_3SiF_2$, Cl, Br, I, CN, NCO, NCS, $NO_3$ and $N_3$.

Sulfonium salts are well known in the prior art. Preferred sulfonium salts of the formula $(R^1R^2N)(R^3R^4N)(R^5R^6N)S^+X^-$ are disclosed in U.S. Pat. No. 3,940,402. In the present application, it is indicated that the term "sulfonium salt" is also inclusive of complexes. Illustratively, the salts of U.S. Pat. No. 3,940,402 can be considered as complexes.

The reaction of hexafluoropropylene epoxide with a ketone or acid fluoride may be undertaken in the liquid phase in the presence of an organic polar solvent of sufficient polarity to dissolve hexafluoropropylene epoxide. The solvent is inert to the reaction and should be a liquid at the temperature and pressure employed. Suitable solvents include aliphatic polyethers with four to 6 carbon atoms and hydrocarbon nitriles with two to 10 carbon atoms, such as the dimethyl ether of diethylene glycol, dioxane, propionitrile, benzonitrile and acetonitrile. Other solvents which are not nitriles or polyethers include dimethyl sulfoxide, N-methyl pyrrolidone, nitroethane and tetrahydrofuran.

The general reaction conditions such as temperature and pressure are not considered critical and may be varied within wide ranges. A reaction temperature of $-80°$ to $200°$ C. is satisfactory with a preferred range of $-30°$ to $100°$ C. Additionally, the pressure in the reaction procedure is not critical to obtain the desired dimer and may range from below atmospheric pressure to several hundred atmospheres. The temperature and pressure is chosen to avoid loss of the hexafluoropropylene epoxde, e.g., by evaporation.

The catalyst concentration of sulfonium salt likewise is not critical to obtain the dimerization of hexafluoropropylene epoxide. Generally, the concentration of catalyst is at least 0.01% by weight of the hexafluoropropylene epoxide. It would be wasteful to use more than 10%.

The present process is considered to follow the direct teachings of U.S. Pat. No. 3,250,808 in the reaction of hexafluoropropylene epoxide with a ketone of acid fluoride. The disclosure of this patent is incorporated by reference herein in relationship to the reaction conditions directed to use of a monovalent metal fluoride catalyst (e.g., catalyst concentration, solvent, temperature and pressure).

The fluorocarbon ethers of the formula

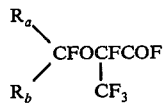

(with $R_a$ and $R_b$ as previously defined) are useful intermediates in formation of surfactants, lubricants and polymers. For purposes of illustration, the ethers may be end-capped and directly employed as surfactants. Additionally, the fluorocarbon ethers may be converted to ethers containing vinyl unsaturation by known techniques, e.g. heating with sodium carbonate. These vinyl ethers may be copolymerized to form useful polymers. In the case of sulfonyl containing vinyl ethers the polymers derived therefrom are highly desirable as ion exchange polymers by conversion of the sulfonyl groups to ion exchange groups. The formation of polymers including ion exchange polymers is known in the prior art.

To further illustrate the present invention, the following exchanges are provided.

EXAMPLE 1

A 320 stainless steel tube was charged with 2.0 g. of

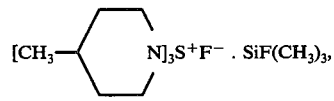

trimethylfluorosilane complex of tris-4-methylpiperidinosulfonium fluoride, 30 ml. of acetonitrile, 42 g. of trifluoroacetyl fluoride and 60 g. of hexafluoropropylene epoxide. The reaction mixture was heated at $30°$ C. for 2 hours. The volatile fraction contained unreacted trifluoroacetyl fluoride and perfluoropropionyl fluoride. The lower fluorocarbon layer of the liquid product weighing 10.0 g. was separated. Gas chromatographic and infrared analysis showed the layer to contain mostly perfluoro-2-ethoxypropionyl fluoride and hexafluoropropylene epoxide dimer in the ratio of 1.43 to 1.0. Further proof of structure was obtained by conversion of the perfluoro-2-ethoxypropionyl fluoride to methyl perfluoro-2-ethoxypropionate by reaction with methanol.

EXAMPLE 2

To a round bottom flask fitted with a magnetic stirrer, thermometer, gas inlet tube, dry ice cooled condenser and saturated with nitrogen were added 30 ml. acetonitrile, 1.4 g. $[(CH_3)_3N]_3S^+F^-.FSi(CH_3)_3$, (trimethylfluorosilane complex of tris-dimethylaminosulfonium fluoride) and 32.6 g. of perfluorovaleryl fluoride. An exothermic reaction took place when hexafluoropropylene epoxide was bubbled into the reaction mixture. After the addition of 20.0 g. of the epoxide at $30°-35°$ C., the reaction mixture was allowed to cool and a lower fluorocarbon layer weighing 47.2 g. was separated. Gas chromatographic analysis showed the layer to contain 59 percent perfluoro-2-n-pentoxypropionyl fluoride as well as hexafluoropropylene epoxide dimer, trimer and unreacted perfluorovaleryl fluoride. Distillation yielded 16.3 g. of chromatographically pure perfluoro-2-n-pentoxypropionyl fluoride, b.p. $101°$ C. [U.S. Pat. No. 3,250,808 b.p. $101°-103°$ C.]. The structure of this compound was further confirmed by NMR and IR spectroscopy and by reaction with methanol to give methylperfluoro-2-n-pentoxypropionate, b.p. $144°$ C. The structure of the latter was confirmed by NMR and IR spectroscopy and by hydrolysis to sodium perfluoro-2-n-pentoxypropionate by heating with aqueous sodium hydroxide followed by pyrolysis of the dry salt to give perfluoro-[n-pentyl vinyl] ether, b.p. $86°$ C. The structure of this compound was confirmed by NMR, IR and mass spectrometry and by reaction with bromine to yield perfluoro-n-pentyl-1,2-dibromo-1,2,2-trifluoroethyl ether, b.p. $152°$ C. The structure of the latter was confirmed by NMR spectroscopy.

EXAMPLE 3

Using the method of Example 1, 1.4 g. $[(CH_3)_2N]_3S^+.F^-.SiF(CH_3)_3$, (trimethyl fluorosilane complex of tris-dimethylamine sulfonium fluoride), 30 ml. of acetonitrile, 47 g. of fluorosulfonyldifluoroacetyl fluoride and 80 g. of hexafluoropropylene epoxide were heated at 50° C. for 3 hours. After bleeding, the volatiles 86 g. of a lower fluorocarbon layer was separated. Gas chromatographic analysis showed three major components, hexafluoropropylene epoxide dimer, $FSO_2F_2CF_2OCF(CF_3)COF$ and $FSO_2CF_2CF_2OCF(CF_3)CF_2OCF(CF_3)COF$ in the ratio of 1.00 to 2.54 to 1.22.

EXAMPLE 4

Using the method of Example 1, 1.6 g. $[(CH_3)_2N]S^+F^-\cdot SiF(CH_3)_3$, 60 ml. diethylene glycoldimethyl ether, 30 ml. acetonitrile, 47 g. $FSO_2CF_2COF$, and 80 g. hexafluoropropylene epoxide were heated at 50° C. for 1 hour and 60° C. for 2 hours. A lower fluorocarbon weighing 115.4 g. was obtained. Gas chromatographic analysis showed the presence of hexafluoropropylene epoxide dimer, $FSO_2CF_2CF_2OCF(CF_3)COF$, HFPO trimer, $FSO_2CF_2CF_2OCF(CF_3)CFOCF(CF_3)COF$ and $FSO_2CF_2CF_2OCF(CF_3)CF_2OCF(CF_3)CF_2OCF(CF_3)COF$ in the ratio of 1.00 to 0.39 to 0.17 to 1.90 to 0.19.

EXAMPLE 5

Using the method of Example 1, 2.0 g. $(CH_3)_3S^+I^-$ [trimethylsulfonium iodide], 30 ml. of acetonitrile and 40 g. each of hexafluoroacetone and hexafluoropropylene epoxide were shaken at 25° C. for 3 hours. The volatiles were bled off and the lower clear fluorocarbon layer distilled to give 62.8 g. of $C_3F_7OCF(CF_3)COF$, boiling point 56° C. Gas chromatographic analysis showed this to be greater than 99 percent $(CF_3)_2CFOCF(CF_3)COF$.

What is claimed is:

1. In a process for the catalytic reaction of hexafluoropropylene epoxide with a compound of the formula

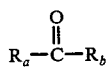

wherein $R_a$ and $R_b$ each independently of the other is fluorine, a fluoroalkyl group of one to 14 carbon atoms, a sulfonyl substituted fluoroalkyl group of one to 14 carbon atoms, a fluoroalkoxy group of one to 14 carbon atoms, a sulfonyl substituted fluoroalkoxy group of one to 14 carbon atoms, a fluoroalkoxyalkyl group of one to 14 carbon atoms and one to six oxygen atoms or a sulfonyl substituted fluoroalkoxyalkyl radical of one to 14 carbon atoms and one to six oxygen atoms, the improvement comprising employing a catalyst having the formula $R_1R_2R_3S^+X^-$, wherein $R_1$, $R_2$ and $R_3$ each independently of the other denotes an alkyl group of one to 20 carbon atoms and X, is selected from the group consisting of F, $(CH_3)_3SiF_2$, Cl, Br, I, CN, NCO, NCS, $NO_2$ and $N_3$.

2. The process of claim 1 wherein said alkyl group is one of five carbon atoms.

3. The process of claim 1 wherein X, is fluorine.

4. In a process for the catalytic reaction of hexafluoropropylene epoxide with a compound of the formula

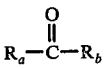

wherein $R_a$ and $R_b$ each independently of the other is fluorine, a fluoroalkyl group of one to 14 carbon atoms, a sulfonyl substituted fluoroalkyl group of one to 14 carbon atoms, a fluoroalkoxy group of one to 14 carbon atoms, a sulfonyl substituted fluoroalkoxy group of one to 14 carbon atoms, a fluoroalkoxyalkyl group of one to 14 carbon atoms and one to six oxygen atoms or a sulfonyl substituted fluoroalkoxyalkyl radical of one to 14 carbon atoms and one to six oxygen atoms, the improvement comprising employing a catalyst having the formula $(R^1R^2N)(R^3R^4N)(R^5R^6N)S^+X^-$ wherein the R groups individually are alkyl of up to 20 carbon atoms, each alkyl having at least 2 -alpha-hydrogen atoms, with the proviso that any or all of the pairs $R^1$ and $R^2$, $R^3$ and $R^4$, and $R^5$ and $R^6$ taken together with the nitrogen atom to which they are attached form a pyrrolidino or piperidino ring, any substituents being alkyl of up to 8 carbon atoms, and X is selected from the group consisting of $(CH_3)_3SiF_2$, Cl, Br, I, CN, NCO, NCS, $NO_2$ and $N_3$.

5. In a process for the catalytic reaction of hexafluoropropylene epoxide with a compound of the formula

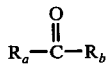

wherein $R_a$ and $R_b$ each independently of the other is fluorine, a fluoroalkyl group of one to 14 carbon atoms, a sulfonyl substituted fluoroalkyl group of one to 14 carbon atoms, a fluoroalkoxy group of one to 14 carbon atoms, a sulfonyl substituted fluoroalkoxy group of one to 14 carbon atoms, a fluoroalkoxyalkyl group of one to 14 carbon atoms and one to six oxygen atoms or a sulfonyl substituted fluoroalkoxyalkyl radical of one to 14 carbon atoms and one to six oxygen atoms, the improvement comprising employing a catalyst having the formula $(R^1R^2N)(R^3R^4N)(R^5R^6N)S^+X^-$ wherein the R groups individually are alkyl of up to 20 carbon atoms, each alkyl having at least 2 alpha-hydrogen atoms, and X is selected from the group consisting of $(CH_3)_3SiF_2$, Cl, Br, I, CN, NCO, NCS, $NO_2$ and $N_3$.

6. In a process for the catalytic reaction of hexafluoropropylene epoxide with a compound of the formula

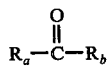

wherein $R_a$ and $R_b$ each independently of the other is fluorine, a fluoroalkyl group of one to 14 carbon atoms, a sulfonyl substituted fluoroalkyl group of one to 14 carbon atoms, a fluoroalkoxy group of one to 14 carbon atoms, a sulfonyl substituted fluoroalkoxy group of one to 14 carbon atoms, a fluoroalkoxyalkyl group of one to 14 carbon atoms and one to six oxygen atoms or a sulfonyl substituted fluoroalkoxyalkyl radical of one to 14 carbon atoms and one to six oxygen atoms, the improvement comprising employing a catalyst having the formula $(R^1R^2N)(R^3R^4N)(R^5R^6N)S^+X^-$ wherein each of the groups $R^1R^2N$, $R^3R^4N$ and $R^5R^6N$ is dimethylamino, and X is selected from the group consisting of $(CH_3)_3SiF_2$, Cl, Br, I, CN, NCO, NCS, $NO_2$ and $N_3$.

* * * * *